(12) United States Patent
Bosworth et al.

(10) Patent No.: US 12,201,290 B2
(45) Date of Patent: Jan. 21, 2025

(54) MULTIPLE SUTURE PASSING DEVICE

(71) Applicant: CONMED CORPORATION, Utica, NY (US)

(72) Inventors: Adrian Bosworth, Bradenton, FL (US); Peter Miller, Largo, FL (US)

(73) Assignee: CONMED CORPORATION, Utica, NY (US)

( * ) Notice: Subject to any disclaimer, the term of this patent is extended or adjusted under 35 U.S.C. 154(b) by 312 days.

(21) Appl. No.: 16/649,677

(22) PCT Filed: Jun. 26, 2018

(86) PCT No.: PCT/US2018/039406
§ 371 (c)(1),
(2) Date: Mar. 23, 2020

(87) PCT Pub. No.: WO2019/005733
PCT Pub. Date: Jan. 3, 2019

(65) Prior Publication Data
US 2021/0369263 A1  Dec. 2, 2021

Related U.S. Application Data

(60) Provisional application No. 62/549,180, filed on Aug. 23, 2017, provisional application No. 62/549,121, (Continued)

(51) Int. Cl.
*A61B 17/04* (2006.01)
*A61B 17/06* (2006.01)
*A61B 17/062* (2006.01)

(52) U.S. Cl.
CPC ...... *A61B 17/0469* (2013.01); *A61B 17/0491* (2013.01); *A61B 17/06004* (2013.01); *A61B 17/0625* (2013.01); *A61B 2017/06042* (2013.01)

(58) Field of Classification Search
CPC ............ A61B 17/0469; A61B 17/0491; A61B 17/06004; A61B 17/0625;
(Continued)

(56) References Cited

U.S. PATENT DOCUMENTS 8,469,974 B2   6/2013   Skinlo et al.
9,198,655 B2   12/2015  Skinlo et al.
(Continued)

FOREIGN PATENT DOCUMENTS

EP   1629780   3/2006
EP   2453809   5/2012

OTHER PUBLICATIONS

Chinese Office Action application No. 201880055214.5, dated May 13, 2023, pp. 1-6.

*Primary Examiner* — Katherine M Shi
*Assistant Examiner* — Mohammed S Adam
(74) *Attorney, Agent, or Firm* — Bond, Schoeneck & King, PLLC; Frederick J. M. Price

(57) ABSTRACT

A system and method for completing one or more stitches without withdrawal and reloading of an inserter. A suture passer includes a distal end having a body with a gripping portion and a suture holding portion. The gripping portion and the suture holding portion are spaced, defining a recess in the body there between. A tube of the gripping portion extends toward the suture holding portion and maintains a needle therein. The needle is slidable within the tube between a retracted position and an extended position. The needle has a notch at its distal end for catching and securing a limb of suture. In the retracted position, the distal end of the needle is within the tube of the gripping portion and in the extended position, the distal end of the needle extends into the suture holding portion.

20 Claims, 21 Drawing Sheets

Related U.S. Application Data filed on Aug. 23, 2017, provisional application No. 62/524,776, filed on Jun. 26, 2017.

(58) Field of Classification Search
CPC .... A61B 2017/06042; A61B 17/06061; A61B 17/0482; A61B 17/0483; A61B 2017/0474

See application file for complete search history.

(56) References Cited

U.S. PATENT DOCUMENTS

| | | |
|---|---|---|
| 10,058,325 B2 | 8/2018 | Weber et al. |
| 2009/0062819 A1* | 3/2009 | Burkhart ............ A61B 17/0469 606/148 |
| 2011/0028998 A1* | 2/2011 | Adams ............... A61B 17/0482 606/145 |

* cited by examiner

MULTIPLE SUTURE PASSING DEVICE

CROSS-REFERENCE TO RELATED APPLICATIONS

The present application claims priority to U.S. Provisional App. No. 62/524,776, filed on Jun. 26, 2017, U.S. Provisional App. No. 62/549,121, filed on Aug. 23, 2017 and U.S. Provisional App. No. 62/549,180, filed on Aug. 23, 2017.

BACKGROUND OF THE INVENTION

1. Field of the Invention

The invention relates generally to a passing suture device and more particularly, to a multiple stitch passing suture device for completing a stitch without withdrawal and reloading of the inserter.

2. Description of Related Art

In order to gain intra-articular access to the hip joint for arthroscopic repair of certain hip pathologies, a surgical incision through the hip's capsule, also known as a capsulotomy, is required. After repair of the pathology, it is often desirable to repair and close the capsular incision to restore its anatomical function. This technique requires the passing of sutures through each leaflet of the incision and the tying of surgical knots to stitch it closed. Other suture passing devices currently available have to be completely withdrawn from the hip joint in order to be reloaded with suture at the device's distal end for each stitch. A more efficient method is needed to complete the stitch.

Therefore, there is a need for a system and method for completing the stitch without the additional steps of withdrawal and reloading the inserter instrument.

SUMMARY OF THE INVENTION

The present invention is directed to, inter alia, a system and method for completing one or more stitches without withdrawal and reloading of the inserter. In one embodiment, the present invention is a suture passer. The suture passer includes a distal end having a body with a gripping portion and a suture holding portion. The gripping portion and the suture holding portion are spaced, defining a recess in the body therebetween. A tube of the gripping portion extends toward the suture holding portion and maintains a needle therein. The needle is slidable within the tube between a retracted position and an extended position. The needle has a notch at its distal end for catching and securing a limb of suture. In the retracted position, the distal end of the needle is within the tube of the gripping portion and in the extended position, the distal end of the needle extends into the suture holding portion. In an alternative embodiment, the present invention is a loaded suture passer. The loaded suture passer additionally includes a suture extending between a first side of the suture holding portion and a second side of the suture holding portion.

In one embodiment, the present invention is a method for passing suture through an object. The method comprises the steps of: (i) providing a distal end of the suture passer having a body with a gripping portion and a suture holding portion, wherein the gripping portion and the suture holding portion are spaced, defining a recess in the body therebetween, a tube of the gripping portion extending toward the suture holding portion, a needle slidable within the tube from a retracted position to an extended position, the needle having a notch at a distal end, wherein in the retracted position, the distal end of the needle is within the tube of the gripping portion and in the extended position, the distal end of the needle extends into the suture holding portion; (ii) positioning an object having a proximal side and a distal side in the recess between the gripping portion and the suture holding portion; (iii) advancing the tube and the needle through a first stitching location on the proximal side of the object to the distal side of the object; (iv) advancing the distal end of the needle into the suture holding portion; (v) retracting the needle from the suture holding portion; (vi) catching a first limb of suture within the notch on the distal end of the needle; and (vii) retracting the needle within the tube such that the notch on the distal end of the needle abuts the tube, securing the first limb of suture within the notch.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
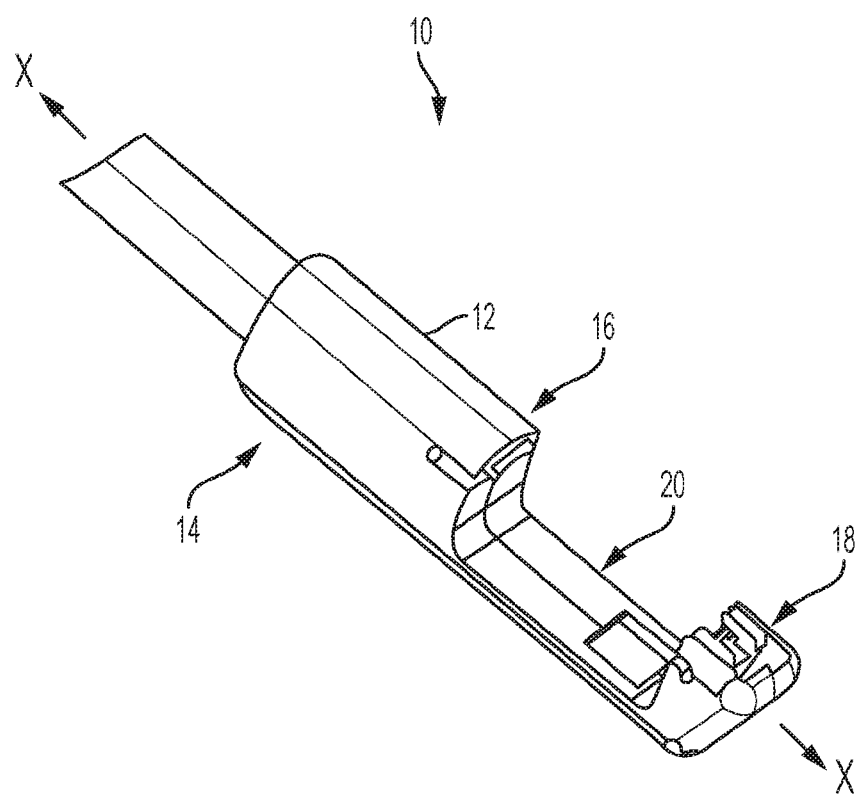
FIG. 1 is a perspective top view schematic representation of a distal end of a suture passing device according to an embodiment.

Referring now to FIG. 1, there is shown a perspective top view schematic representation of a distal end of a suture passing device according to an embodiment. FIG. 1 shows a suture passing device 10 comprising a body 12 which extends along a distal end 14 of the suture passing device 10. In particular, the body 12 extends along a central longitudinal axis x-x of the device 10. The body 12 of the device 10 includes a proximal gripping portion 16 and a distal suture holding portion 18. As shown in FIG. 1, the suture holding portion 18 comprises the most distal portion of the body 12. Further shown in the embodiment of FIG. 1, the griping portion 16 and the suture holding portion 18 are spaced such that there is a recess 20 in the body 12 between the gripping and suture holding portions 16, 18. The recess 20 is configured or otherwise sized such that a tissue, biological body, or other object may be placed between the gripping portion 16 and the suture holding portion 18. As described in detail herein, the gripping portion 16 and the suture holding portion 18 comprise features which facilitate the formation of complete stitches without the withdrawal of the device 10 from the tissue (biological body or object) and reloading of the device 10.

Figure 2:
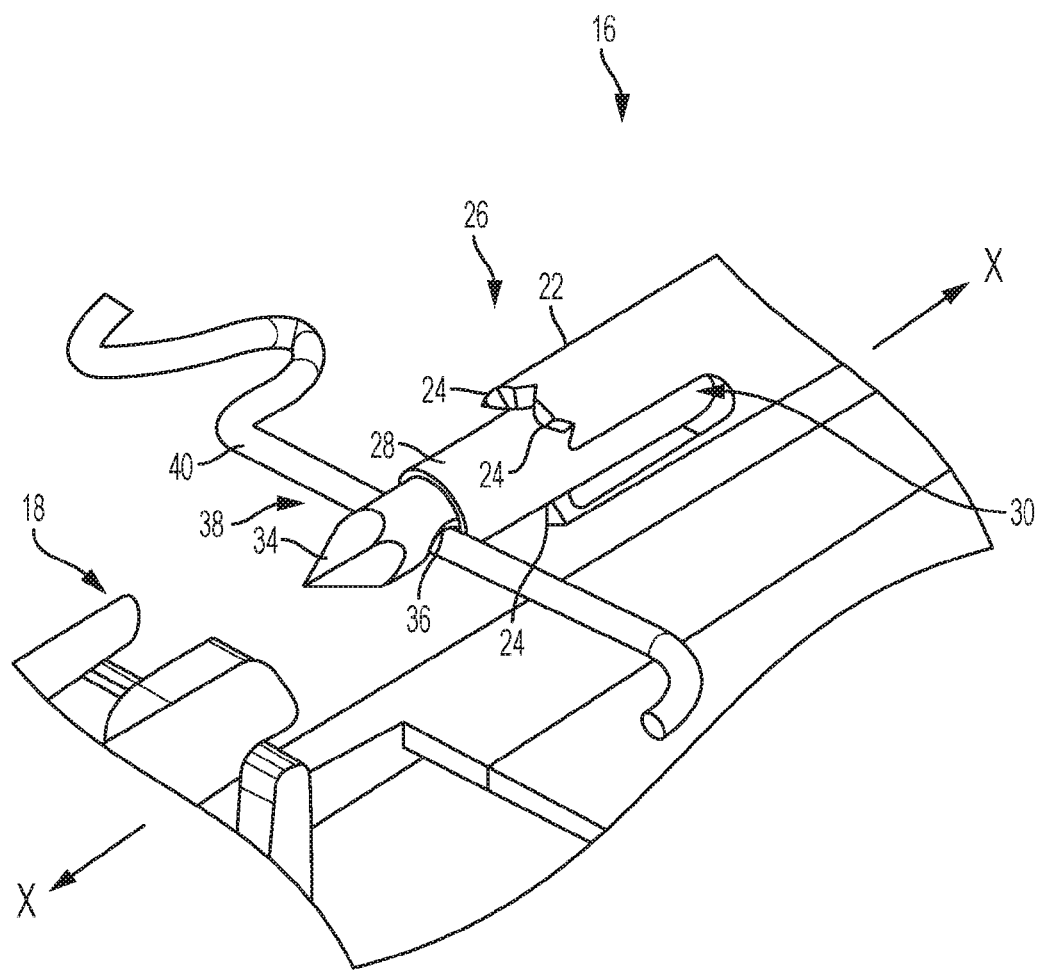
FIG. 2 is a close-up perspective top view schematic representation of the gripping portion of the device in a loaded configuration, between retracted and extended positions, according to an embodiment.

Turning now to FIG. 2, there is shown a close-up perspective top view schematic representation of the gripping portion 16 of the device 10 in a loaded configuration, between retracted and extended positions, according to an embodiment. In the embodiment shown in FIG. 2, the gripping portion 16 comprises a clamp tube 22 which extends distally in a direction substantially parallel to the central longitudinal axis x-x toward the suture holding portion 18. In the depicted embodiment, the clamp tube 22 comprises one or more protrusions 24 at its distal end 26 for engaging a tissue or other biological body in the recess 20. However, the clamp tube 22 may also have a smooth distal end 26 (with no protrusions 24), if desired.

Still referring to FIG. 2, the gripping portion 16 additionally comprises a movable (i.e., slidable) tube or tubular sheath 28 which extends through the clamp tube 22 also in a direction parallel to the central longitudinal axis x-x. The sheath 28 extends at least in a portion of a first inner volume 30 of the clamp tube 22. Further, as also shown in the depicted embodiment, the sheath 28 comprises a second inner volume 32 (not shown), which is configured and otherwise sized for a movable (i.e., slidable) needle 34. As shown in FIG. 2, the needle 34 extends within the second inner volume 32 of the sheath 28 and extends in a direction parallel to the central longitudinal axis x-x. The needle 34 comprises a notch 36 at its distal end 38. The notch 36 is sized or otherwise dimensioned to accommodate a suture 40 (or other comparable stitching material).

As shown in FIG. 2, the needle 34 grabs and secures the suture 40 in the loaded configuration when the suture 40 extends through the notch 36 in the needle 34 and the notch 36 is abutted by the distal end of the sheath 28. The distal end of the sheath 28 holds the suture 40 in place within the adjacent and abutting notch 36. In one embodiment, a tensioning mechanism holds the sheath 28 in place relative to the notch 36 in the loaded configuration. The tensioning mechanism can be a spring within the clamp tube 22, for example.

Figure 3:
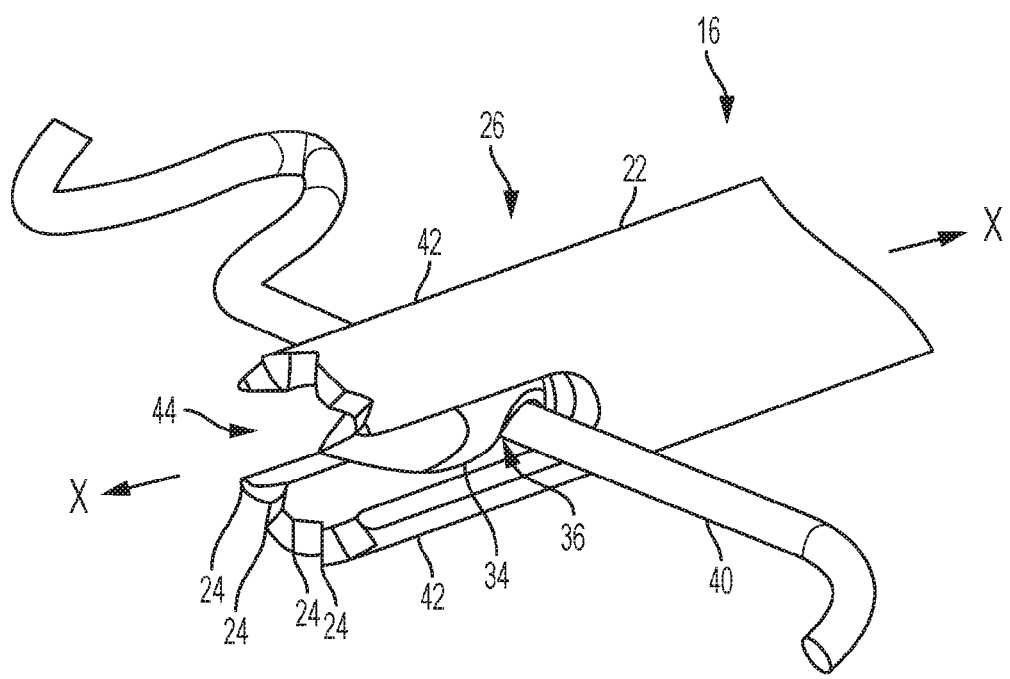
FIG. 3 is a close-up perspective side view schematic representation of the distal end of the clamp tube in the loaded configuration, retracted position, according to an embodiment.

Referring now to FIG. 3, there is shown a close-up perspective side view schematic representation of the distal end 26 of the clamp tube 22 in the loaded configuration, retracted position, according to an embodiment. From the loaded configuration between the retracted and extended positions, shown in FIG. 2, the needle 34 and the sheath 28 are moved proximally along an axis parallel to the central longitudinal axis x-x away from the suture holding portion 18. As the needle 34 and the sheath 28 move proximally, they are withdrawn into clamp tube 22 to a loaded configuration, retracted position, as shown in FIG. 3. In the depicted embodiment, the clamp tube 22 can be forked, having a pair of opposing prongs 42 with opening 44 therebetween. The forked distal end 26 of the clamp tube 22 allows the suture 40 to extend in the openings 44 between the prongs 42 when the needle 34 and the sheath 28 are withdrawn proximally into the clamp tube 22. In the depicted embodiment, the suture 40 extends in a direction approximately perpendicular to the central longitudinal axis x-x within the openings 44 between the prongs 42. Thus, the needle 34 and the sheath 28 can be withdrawn into the clamp tube 22 without disturbing the suture 40.

Figure 4:
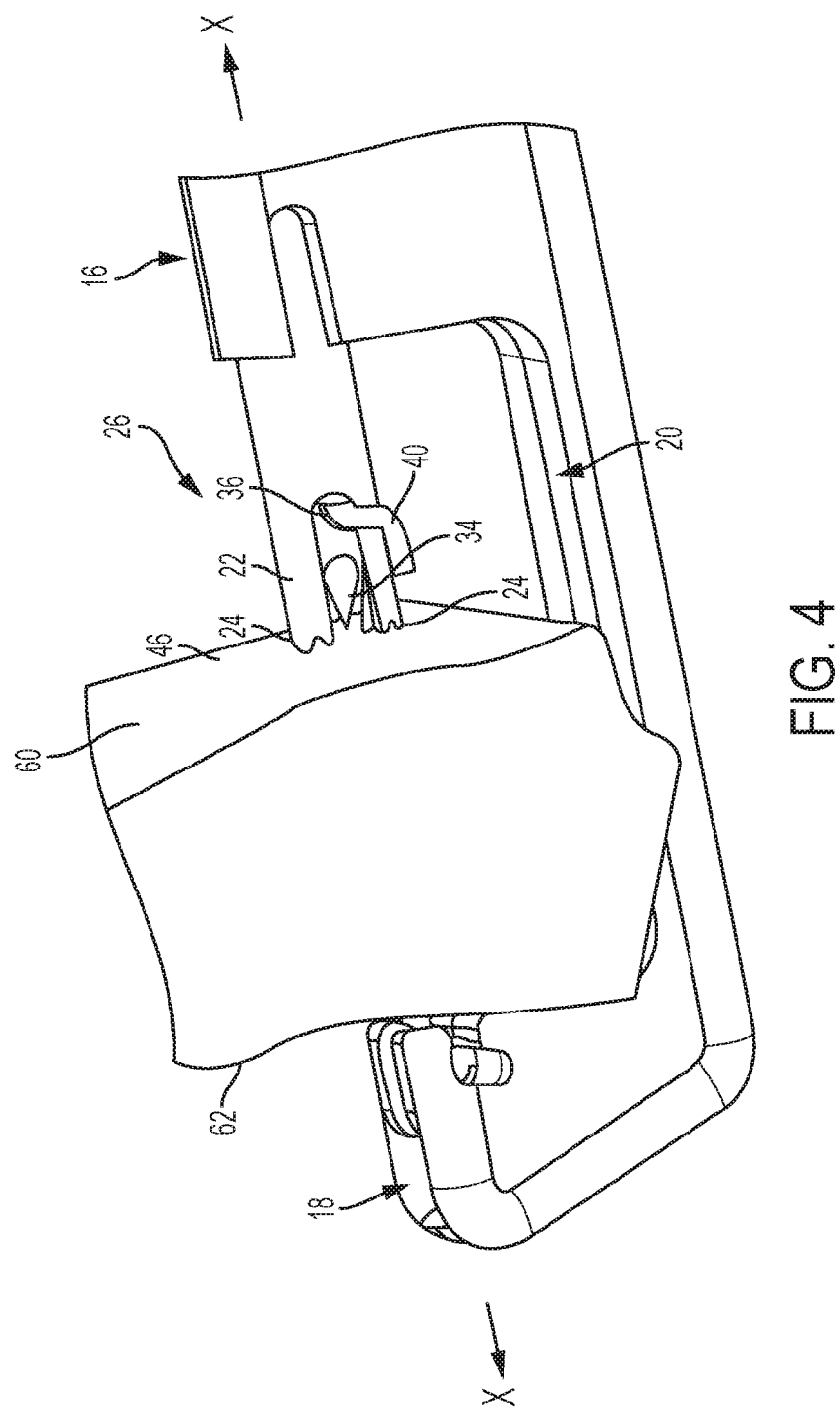
FIG. 4 is a perspective side view schematic representation of the device in the loaded configuration, retracted position around a tissue according to an embodiment.

Turning now to FIG. 4, there is shown a perspective side view schematic representation of the device 10 in the loaded configuration, retracted position around a tissue 46 according to an embodiment. After the suture 40 is loaded into the notch 36 of the needle 34 (FIG. 2) and the needle 34 and sheath 28 are retracted into the clamp tube 22 (FIG. 3), the device 10 can engage a tissue 46 or other biological body for stitching. In the depicted embodiment, a tissue 46 to be stitched is positioned within the recess 20 of the body 12 between the gripping portion 16 and the suture holding portion 18. When the tissue 46 is within the recess 20, the clamp tube 22 is advanced distally along an axis parallel to the central longitudinal axis x-x to contact and engage a first stitching location on the tissue 46. In the depicted embodiment, the protrusions 24 on the distal end 26 of the clamp tube 22 are distally advanced with the clamp tube 22 until the protrusions 24 engage the tissue 46.

Figure 5:
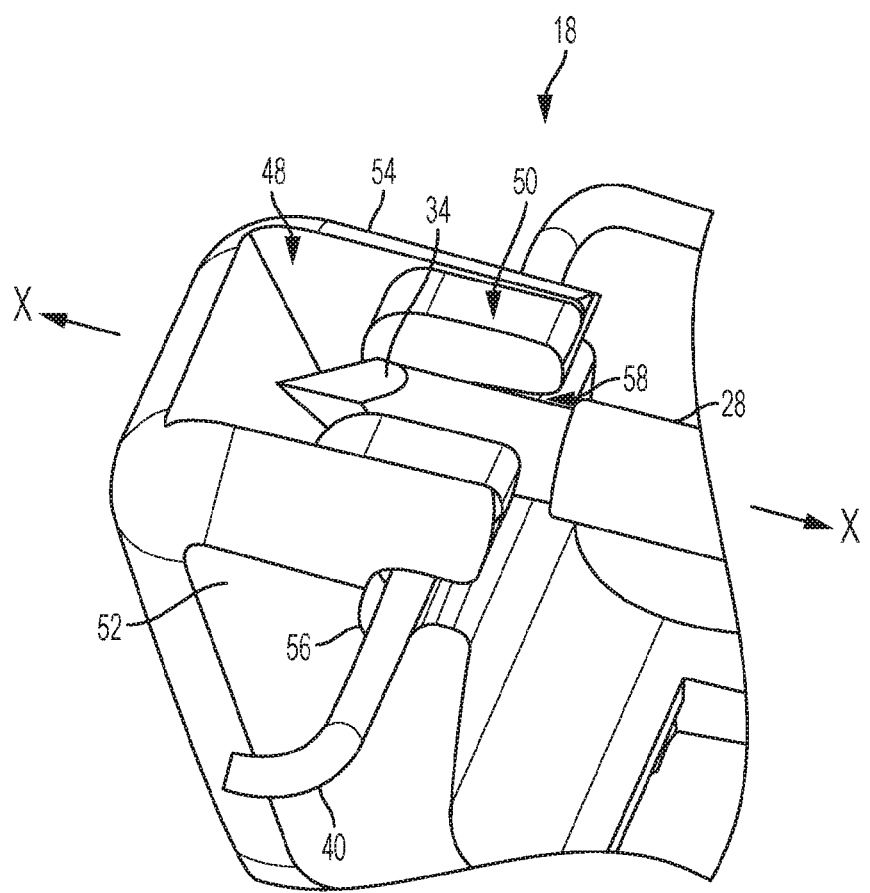
FIG. 5 is a close-up perspective top view schematic representation of the needle in the suture holding portion of the body of the device according to an embodiment

Referring now to FIG. 5, there is shown a close-up perspective top view schematic representation of the needle 34 in the suture holding portion 18 of the body 12 of the device 10 according to an embodiment. The suture holding portion 18 comprises a distal jaw 48 with a toggle gate 50. As shown in FIG. 5, the toggle gate 50 extends between a first side 52 of the distal jaw 48 and a second side 54 of the distal jaw 48. In the depicted embodiment, the distal jaw 48 has a jaw slot 56 which corresponds and aligns with a toggle gate slot 58 in the toggle gate 50 (also shown in FIG. 6).

From the loaded configuration, retracted position shown in FIG. 4, the sheath 28, needle 34, and secured suture 40 are advanced from a proximal side 60 of the tissue 46 through to a distal side 62 of the tissue 46. Once the needle 34 and the sheath 28 extend through the distal side 62 of the tissue 46, the needle 34 and the sheath 28 continue to extend to a loaded configuration, extended position shown in FIG. 5. In the loaded configuration, extended position, the needle 34 extends into the toggle gate 50 between the first and second sides 52, 54 of the distal jaw 48 of the suture holding portion 18. Accordingly, the suture 40 carried by the needle 34 enters the aligned toggle gate slot 58 and jaw slot 56. In the depicted embodiment, a distance that the needle 34 extends distally is greater than a distance at which the sheath 28 extends distally. As a result, in the retracted position, the sheath 28 no longer abuts the notch 36 of the needle 34. In an embodiment wherein the tensioning mechanism is a spring within the clamp tube 22, the spring tension is released between the notch 36 and the sheath 28. As the tension is released, the suture 40 is released from the notch 36, dropping the suture 40 into the toggle gate slot 58 and the jaw slot 56.

Figure 6:
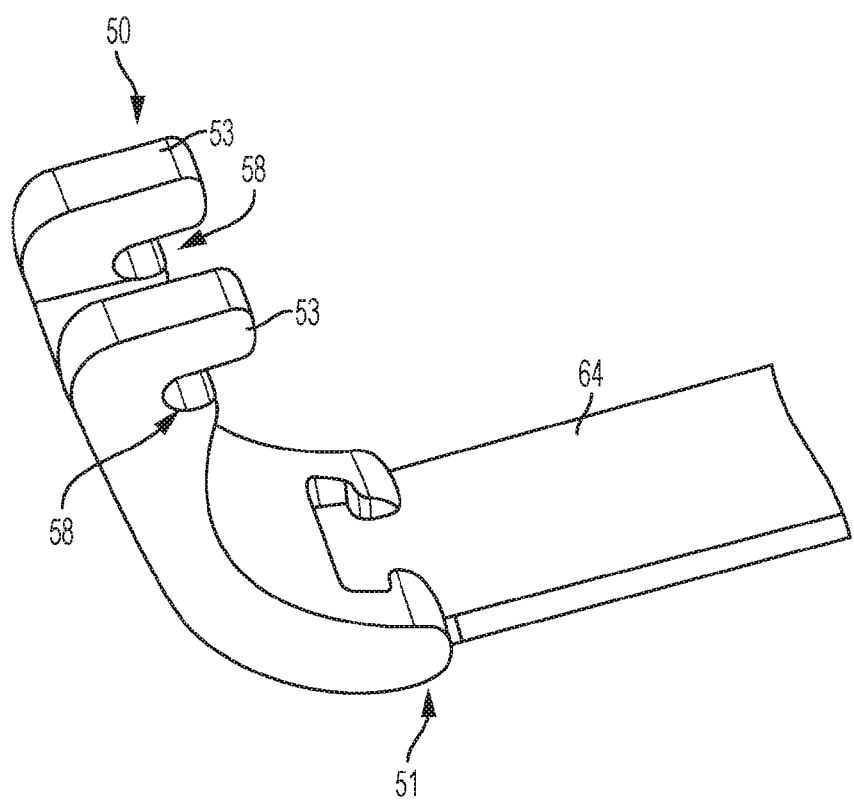
FIG. 6 is a perspective side view schematic representation of the toggle gate of the suture holding portion of the device according to an embodiment.
Figure 7:
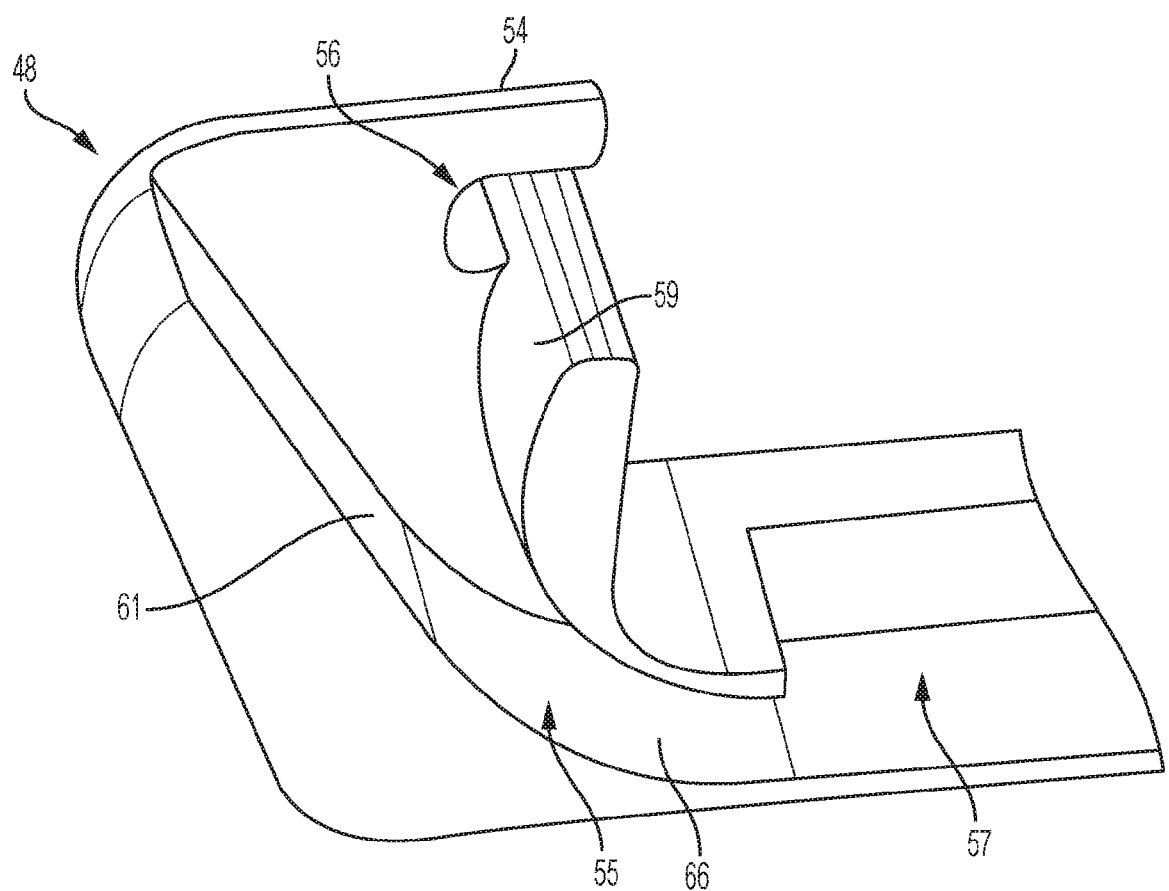
FIG. 7 is a cross-sectional perspective side view schematic representation of the distal jaw of the suture holding portion of the device according to an embodiment.
Figure 8:
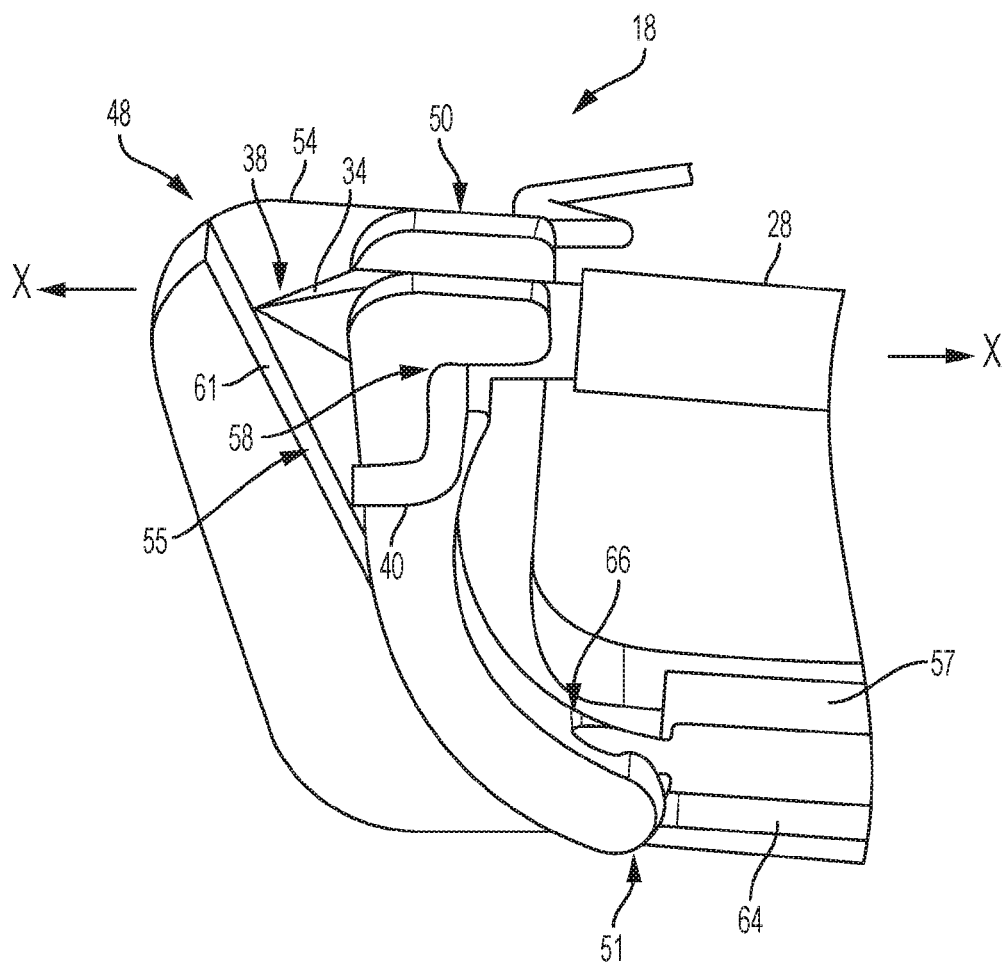
FIG. 8 is a cross-sectional perspective side view schematic representation of the toggle gate in the unlocked state and the needle in the loaded configuration, extended position, according to an embodiment.

Referring now to FIGS. 6-7, there are shown various views schematic representations of the components of the suture holding portion 18 of the device 10 according to an embodiment. As shown in FIG. 6, the toggle gate 50 is connected to an actuator rod 64 via a hinge 51. The actuator rod 64 controls movement of the toggle gate 50 in a rotary track 66 in the distal jaw 48 of the suture holding portion 18. In the depicted embodiment, the toggle gate 50 is curved and comprises a pair of prongs 53 which extend in a direction parallel to the central longitudinal x-x axis when the toggle gate 50 is in the unlocked state (as shown in FIG. 8). The extension of the prongs 53 from the toggle gate 50 defines the toggle gate slot 58, which is configured to receive the suture 40 from the needle 34.

Figure 9:
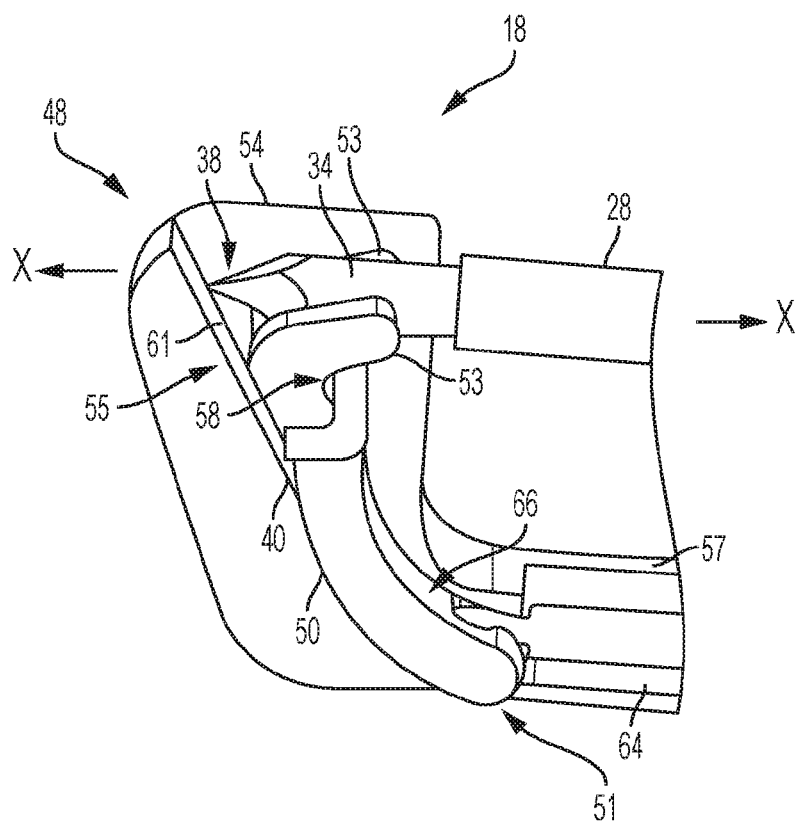
FIG. 9 is a cross-sectional perspective side view schematic representation of the toggle gate in the locked state and the needle in the unloaded configuration, extended position, according to an embodiment.
Figure 10:
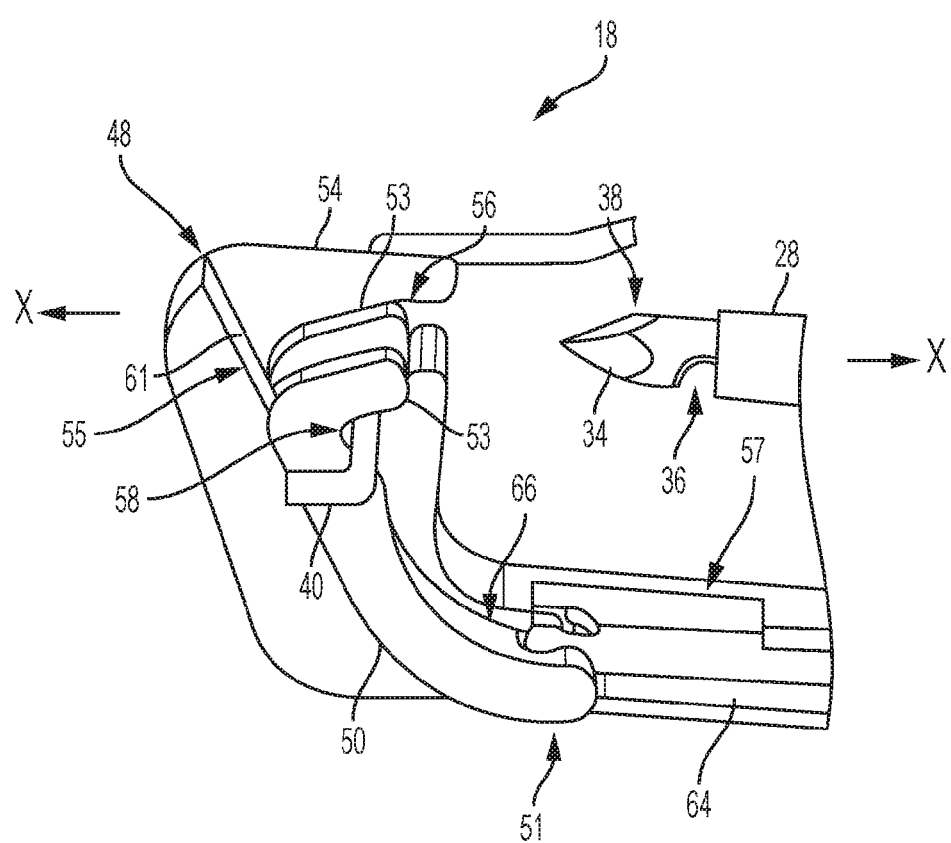
FIG. 10 is a cross-sectional perspective side view schematic representation of the toggle gate in the locked state and the needle in the unloaded configuration, between the retracted and extended positions, according to an embodiment.

FIG. 7 shows a cross-sectional perspective side view of the distal jaw 48 of the suture holding portion 18 of the device 10, according to an embodiment. The rotary track 66 extends between the first side 52 (not shown) and second side 54 of the distal jaw 48. As shown in FIG. 7, the rotary track 66 has a curved portion 55 to accommodate the curved toggle gate 50 and a substantially straight portion 57 to accommodate a substantially straight actuator rod 64. The distal jaw 48 comprises a proximal wall 59 and a distal wall 61 for defining the curved portion 55 of the rotary track 66. The distance between the proximal wall 59 and the distal wall 61 is greater than a width of the toggle gate 50 such that the toggle gate 50 can rotate within the curved portion 55 of the rotary track 66. As shown in FIGS. 8-10, the actuator rod 64 moves the toggle gate 50 in both a clockwise and counterclockwise manner such that the toggle gate 50 moves away from and towards, respectively, the rotary track 66.

Turning now to FIGS. 8-10, there are shown cross-sectional side view schematic representations of the suture holding portion 18 moving from the loaded configuration, extended position toward an unloaded configuration, retracted position. As shown in FIG. 8, the needle 34 extends within the toggle gate 50 in the loaded configuration, extended position. In the loaded configuration, extended position, the toggle gate 50 is in the unlocked state, at its greatest distance from the rotary track 66. The actuator rod 64 is engaged to move the toggle gate 50 from the unlocked state in FIG. 8 to the locked state in FIG. 9. As shown in FIG. 8, the hinge 51 connecting the toggle gate 50 to the actuator rod 64 is within the curved portion 55 of the rotary track 66 when the toggle gate 50 is in the unlocked state. To move the toggle gate 50 to the locked state, the actuator rod 64 is moved or otherwise pulled proximally within the rotary track 66, pulling the hinge 51 into the substantially straight portion 57 of the rotary track 66. In the locked state, the toggle gate 50 is at its smallest distance from the rotary track 66. In the embodiment in FIG. 9, the toggle gate 50 abuts the distal wall 66 of the distal jaw 48 in the locked state. When the toggle gate 50 is in the locked state, the needle 34 and the sheath 28 can be retracted proximally out from suture holding portion 18, as shown in FIG. 10.

Figure 11:
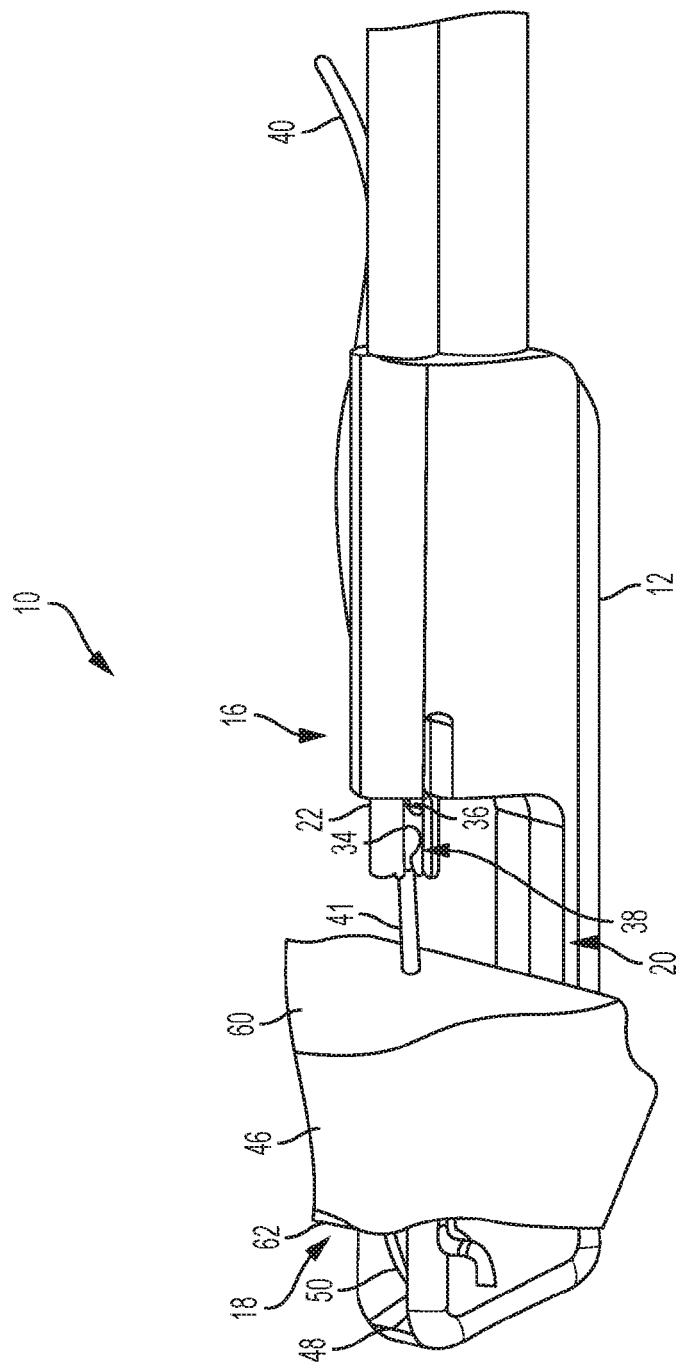
FIG. 11 is a perspective side view schematic representation of the needle in the unloaded configuration, retracted position, according to an embodiment.

Referring briefly now to FIG. 11, there is shown a perspective side view schematic representation of the device 10 in the unloaded configuration, retracted position. As the needle 34 and the sheath 28 moves proximally, as shown in FIG. 10, the needle 34 and the sheath 28 are retracted or withdrawn proximally along an axis parallel to the central longitudinal axis x-x into the clamp tube 22 until the unloaded configuration, retracted position is reached. In the unloaded configuration, retracted position shown in FIG. 11, the needle 34 and the sheath 28 are withdrawn entirely into the clamp tube 22 such that the distal end 38 of the needle 34 is within the clamp tube 22. Also, in the unloaded configuration, retracted position, the tissue 46 remains in the recess 20 in the body 12 between the suture holding portion 18 and the gripping portion 16. As shown, a first limb 41 of suture 40 extends through the tissue 46 and is locked in the toggle gate 50 (in the locked state).

Figure 12:
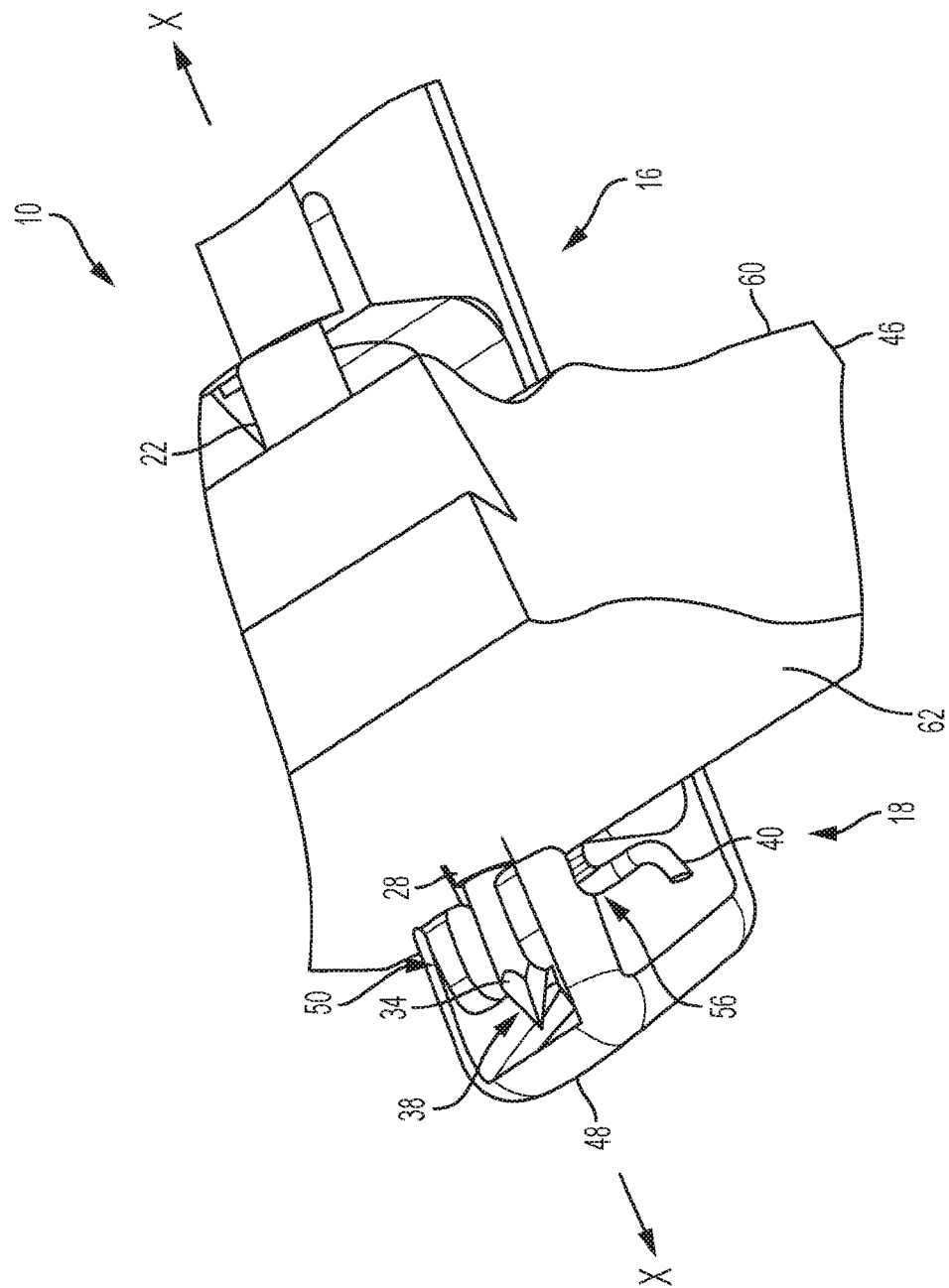
FIG. 12 is a perspective top view schematic representation of the toggle gate in the locked state and the needle in the unloaded configuration, extended position, according to an embodiment.

Turning now to FIG. 12, there is shown a perspective top view schematic representation of the device 10 in the unloaded configuration, extended position. From the unloaded configuration, retracted position shown in FIG. 11, the device 10 is moved along the tissue 46 to a second stitching location. Generally, the second stitching location is adjacent the first stitching location and is close enough to the second stitching location to form a strong connection between the first and second stitching locations. However, the first and second stitching locations cannot be so close that tension on the suture 40 will pull the suture 40 from the first stitching location to the second stitching location. After the device 10 is moved along the tissue 46 to the second stitching location, the clamp tube 22 is extended distally toward the tissue 46 until it engages the tissue 46 at the second stitching location. Thereafter, the needle 34 and the sheath 28 are fully extended distally through the tissue 46 at the second stitching location and into toggle gate 50. In FIG. 12, the toggle gate 50 is in the locked state and the needle 34 is in the unloaded configuration, extended position within the toggle gate 50.

Figure 13:
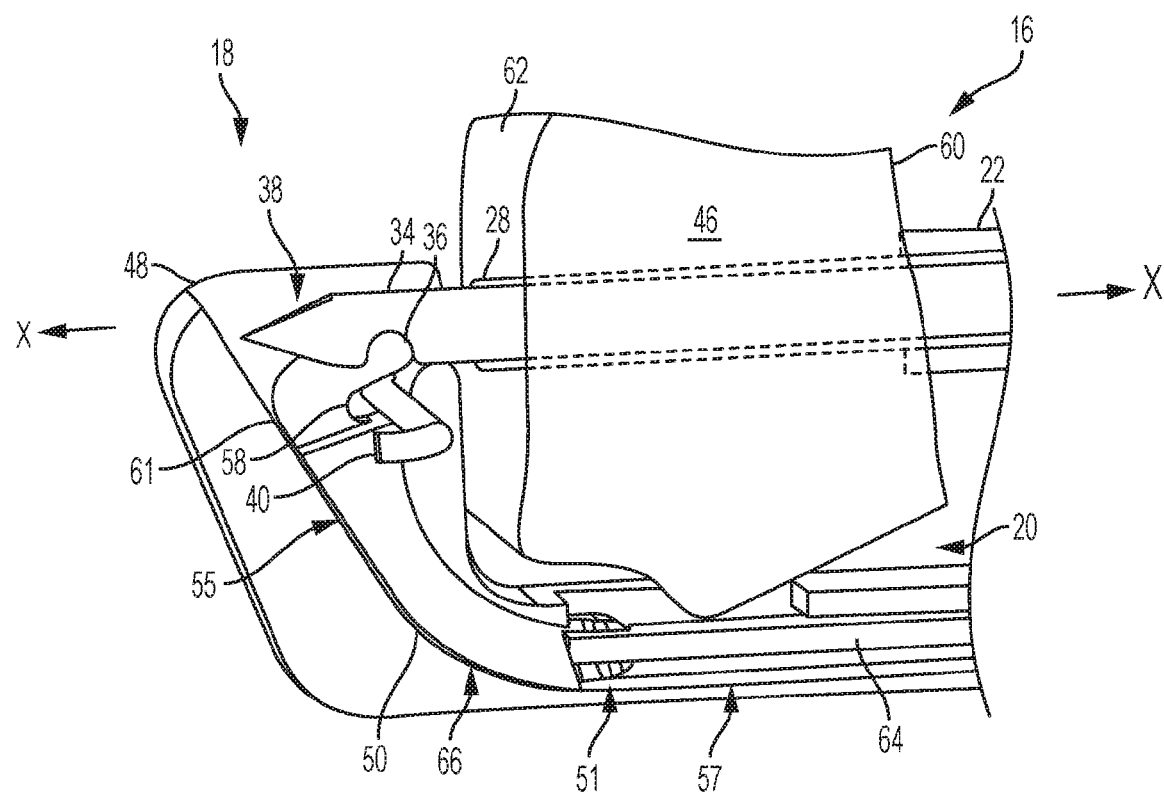
FIG. 13 is a cross-sectional side view schematic representation of the distal end of the device in FIG. 12, according to an embodiment.

Referring now to FIG. 13, there is shown a cross-sectional side view schematic representation of the distal end 14 of the device 10 in FIG. 12. As shown in FIG. 13, the needle 34 and the sheath 28 are fully extended through the distal side 62 of the tissue 46 and into the toggle gate 50. As described above, the toggle gate 50 is in the locked state against the rotary track 66. In the unloaded configuration, extended position, the notch 36 of the needle 34 is positioned above the suture 40 in the toggle gate slot 58 and jaw slot 48 (in the locked state). As shown in the depicted embodiment, the notch 36 is approximately aligned with the suture 40.

Figure 14:
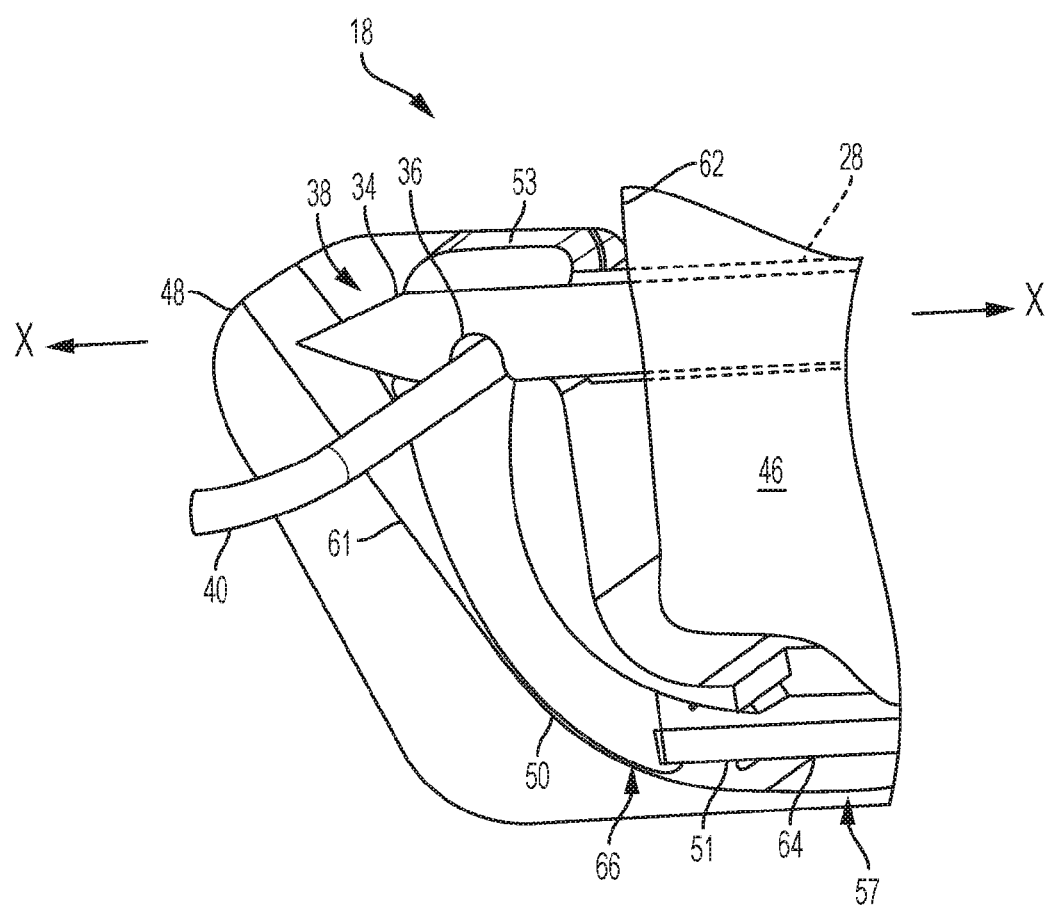
FIG. 14 is a cross-sectional perspective side view schematic representation of the toggle gate in the unlocked state and the needle in the loaded configuration, extended position, according to an embodiment.
Figure 15:
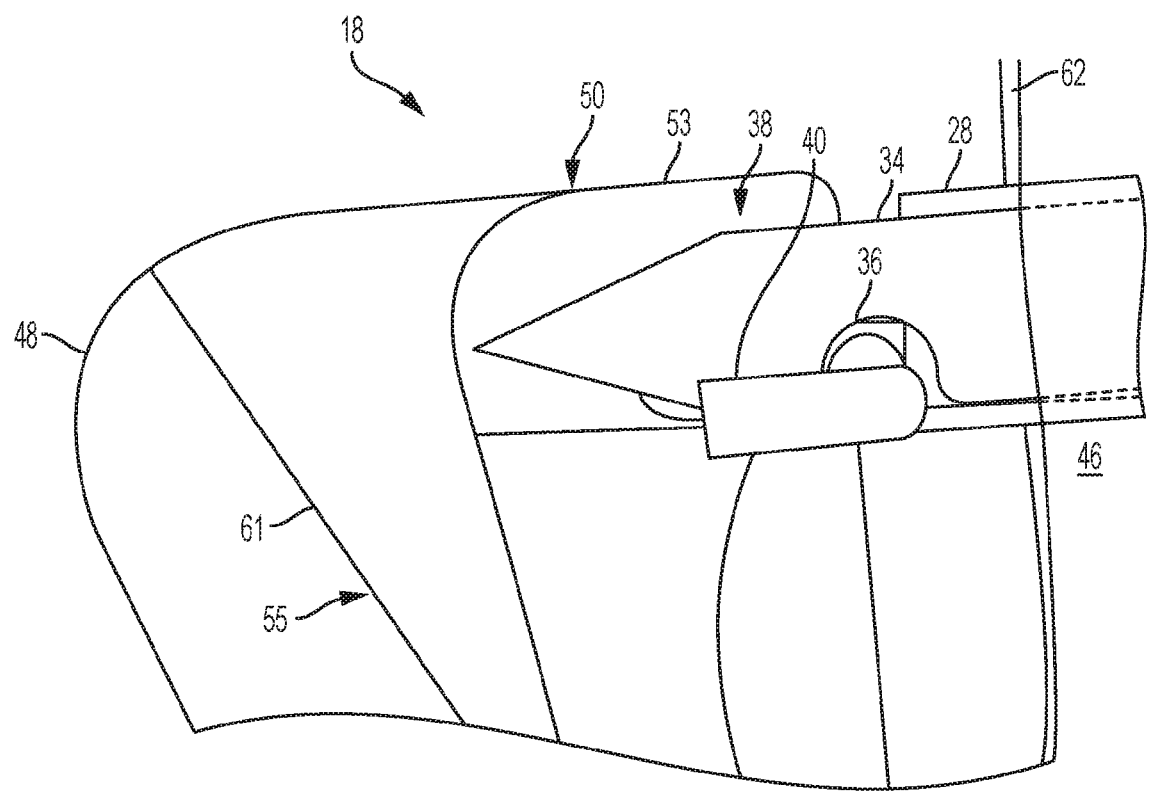
FIG. 15 is a close-up cross-sectional side view schematic representation of the distal end of the needle in FIG. 14.

Turning now to FIG. 14-15, there are shown cross-sectional side view schematic representations of the toggle gate 50 in the unlocked state. From the locked state, shown in FIG. 13, the toggle gate 50 is rotated to the unlocked state in the rotary track 66 through movement of the actuator rod 64 by the surgeon (or other user). When the toggle gate 50 is moved to the unlocked state, the toggle gate 50 moves the suture 40 within the notch 36 of the needle 34, as shown in FIG. 14. The suture 40 is then captured again by the notch 36 as the tension supplied by a tensioning mechanism moves the sheath 28 toward the notch 36, and the sheath 28 and the needle 34 are withdrawn and pulled in the proximal direction toward the distal side 62 of the tissue 46, as shown in FIG. 15.

Figure 16:
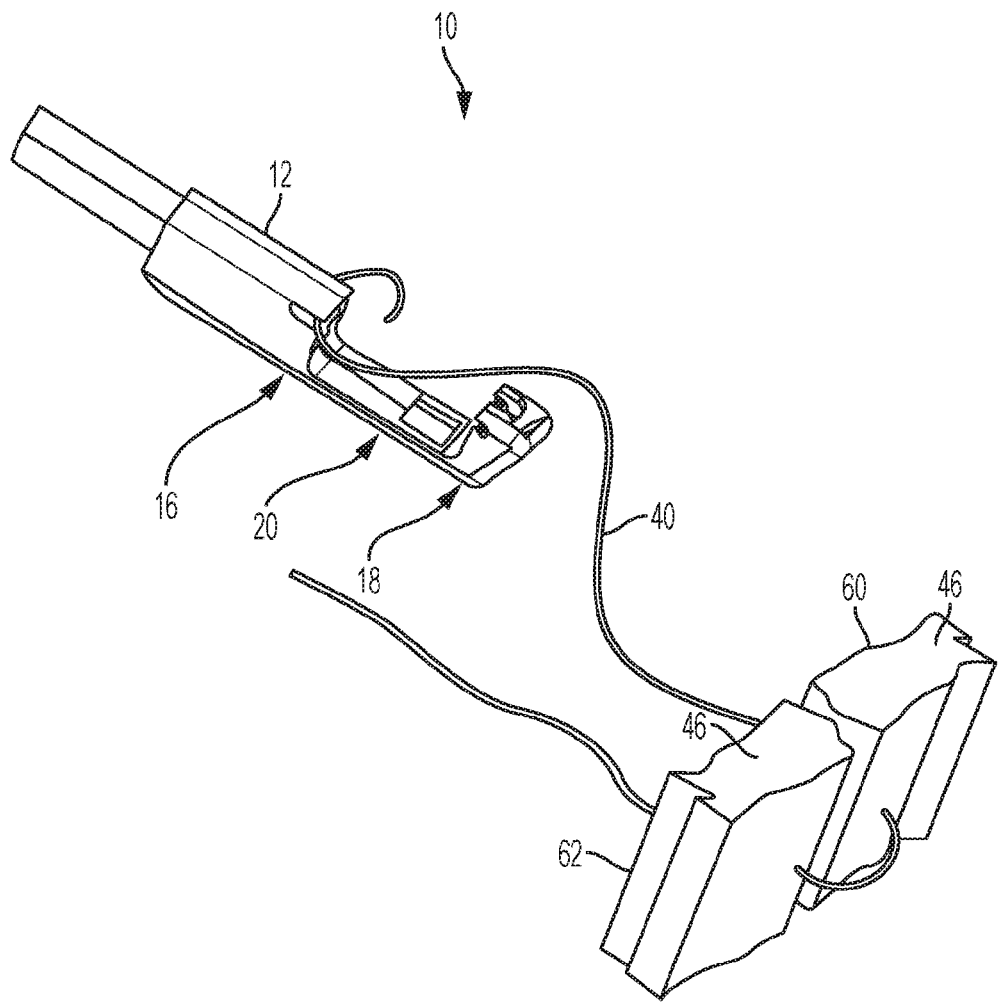
FIG. 16 is a perspective view schematic representation of the needle in the loaded configuration, retracted position and the device removed from the tissue according to an embodiment.

Referring now to FIG. 16, there is shown a perspective view schematic representation of the device 10 in the loaded configuration, retracted position removed from the tissue 46 according to an embodiment. As shown in FIG. 16, the device 10 can be withdrawn from the tissue 46 at the surgical site upon completion of the procedure. For example, a surgeon can complete a mattress stitch at a hip joint using the device 10 followed by the formation of surgical knots to approximate and close the tissue 46 (in FIG. 16). After use of the device 10, the surgeon can withdraw the device 10 from the surgical site at the hip joint, removing the device 10 from the surgical site through a cannula.

Figure 17:
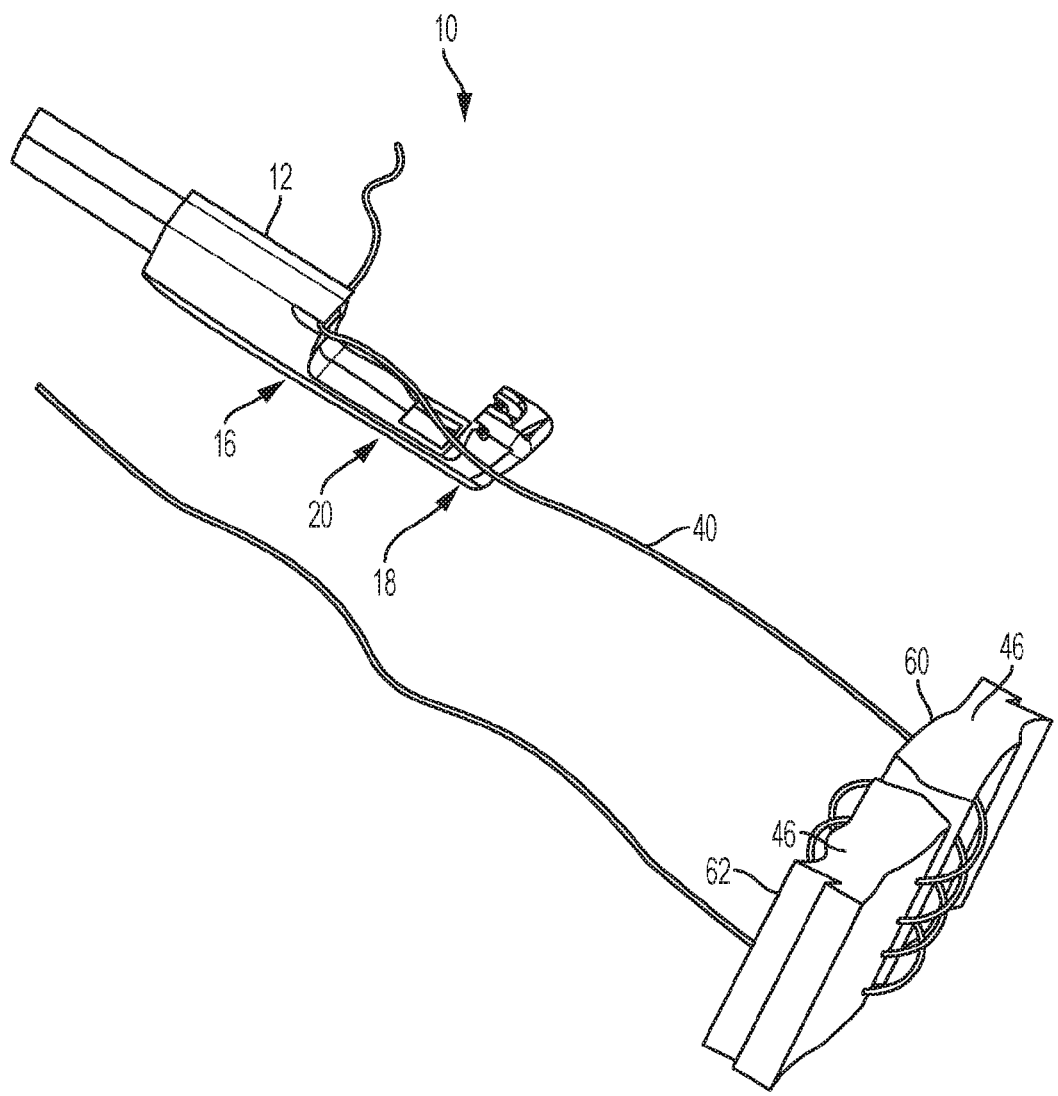
FIG. 17 is a perspective view schematic representation of the needle in the loaded configuration, retracted position and the device removed from the tissue according to another embodiment.

Turning briefly to FIG. 17, there is shown a perspective view schematic representation of the device 10 in the loaded configuration, retracted position removed from the tissue 46 according to another embodiment. In an alternative embodiment, more stitches can be formed if desired by the surgeon. As shown in FIG. 17, more stitches can be formed in the tissue 46 by continuing to move the device 10 (as shown in FIG. 11) to one or more additional stitching locations. Again, after the stitches are formed with the device 10 and the surgical knots are tied to approximate and close the tissue 46, the device 10 can be removed from the surgical site through a cannula.

Figure 18:
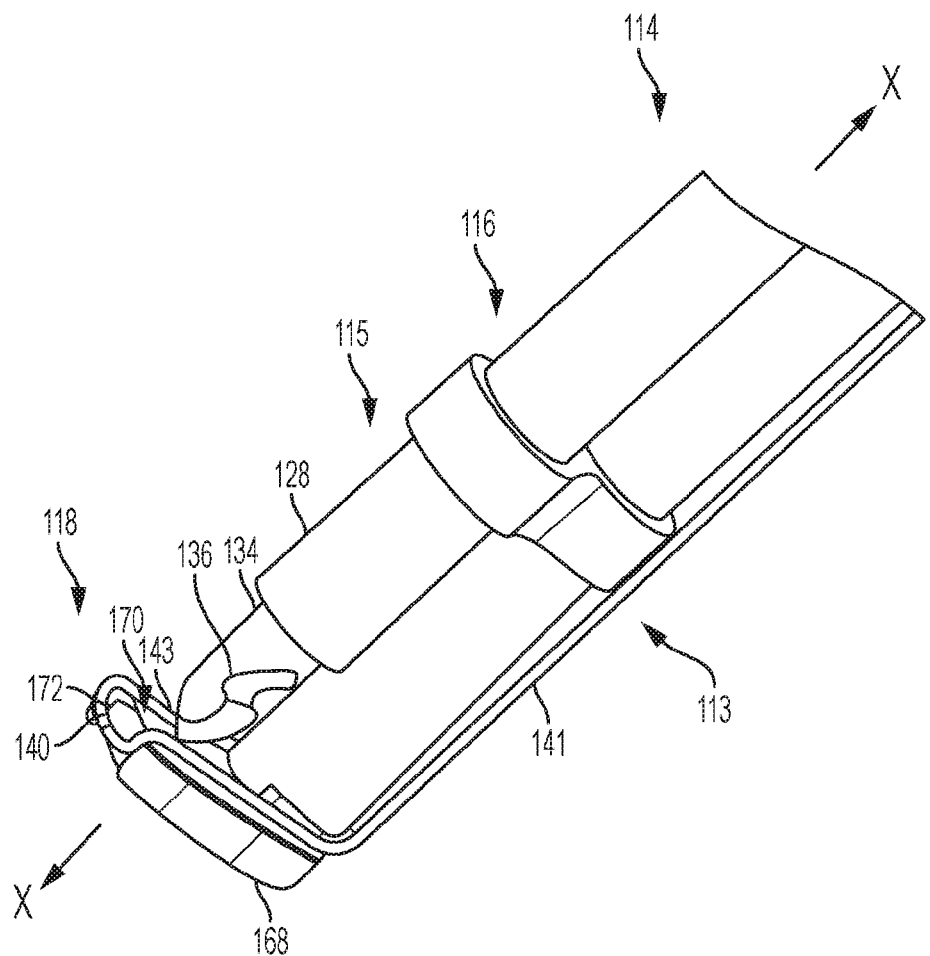
FIG. 18 is a perspective side view schematic representation of the needle in the unloaded configuration, between the retracted and extended positions, according to an alternative embodiment.

Referring now to FIGS. 18-21, there are shown various views schematic representations of an alternative embodiment of the distal end 114 of the device 100. Turning first to FIG. 18, the device 100 comprises a gripping portion 116 with a tubular sheath 128 and a needle 134 having a notch 136, similar to that shown in FIG. 2. In the depicted embodiment, the suture holding portion 118 of the device 100 comprises an end piece 168 extending in a direction substantially perpendicular to the central longitudinal axis x-x. As shown in FIG. 18, the end piece 168 comprises an approximately central aperture 170 extending through the end piece 168. The aperture 170 is substantially aligned with the needle 134 such that the needle 134 may be extended and retracted through the aperture 170.

Still referring to FIG. 18, the suture 140 is loaded onto the end piece 168. The end piece 168 comprises a prong 172 (or other protrusion) extending therefrom. To use the device, the suture 140 is wrapped around the prong 172 such that a first limb 141 of suture 140 extends on a first side 113 of the device 100 and a second limb 143 of suture 140 extends on a second side 115 of the device 100.

Figure 19:
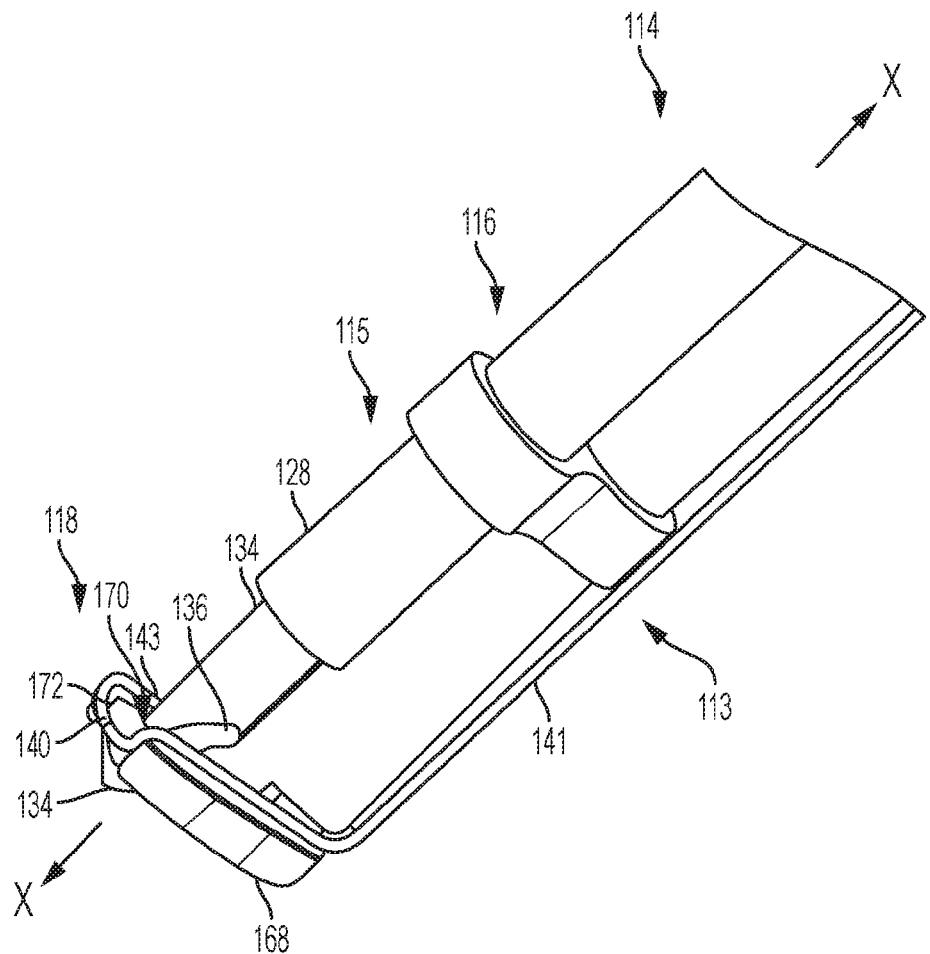
FIG. 19 is a perspective side view schematic representation of the needle in the unloaded configuration, extended position according to an alternative embodiment.
Figure 20:
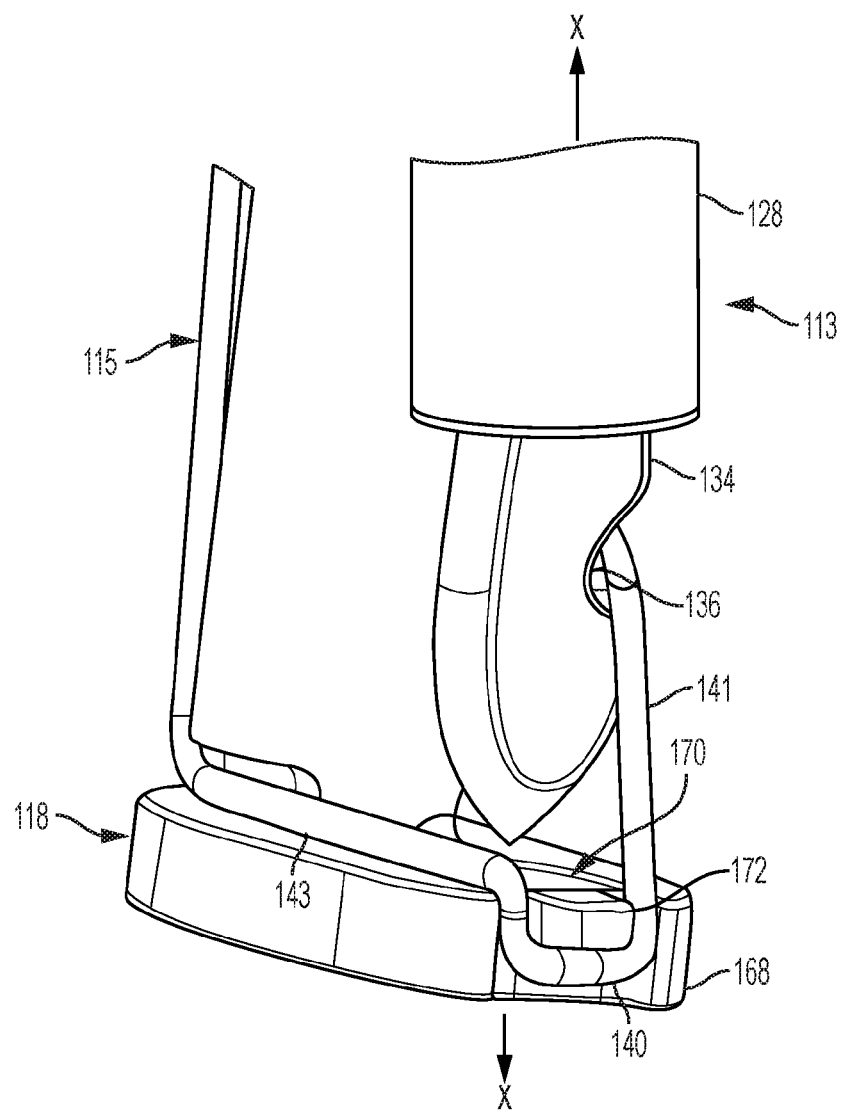
FIG. 20 is a perspective side view schematic representation of the needle in the loaded configuration, between the retracted and extended positions, according to an alternative embodiment.

Turning now to FIG. 19, after the device 100 is in the unloaded configuration between the retracted and extended positions (FIG. 18), the needle 134 is extended through the tissue (not shown for clarity). As shown in FIG. 19, the needle 134 moves through the tissue (not shown) and into the aperture 170 in the end piece 168. In the depicted embodiment, the notch 136 of the needle 134 faces a first direction as the needle 134 extends into the aperture 170. After the needle 134 is full extended in the unloaded configuration, extended position, as shown in FIG. 19, the needle 134 is retracted, as shown in FIG. 20. As the needle 134 is retracted, the notch 136 of the needle 134 catches or grabs the first limb 141 of suture 140. Similar to the device 10 shown in FIGS. 1-17, the sheath 128 of the device 100 in FIG. 20 maintains and secures the first limb 141 of suture 140 within the notch 136 as the needle 134 is retracted. When the needle 134 is retracted, the sheath 128 abuts the notch 136 and secures the first limb 141 within the notch 136. As described above with reference to the device shown in FIGS. 1-17, a tensioning mechanism, such as a spring within the gripping portion 116 of the device 100, tensions the sheath 128 at the notch 136 of the needle 134. The needle 134 is completely withdrawn from the tissue (not shown) to a loaded configuration, retracted position.

Figure 21:
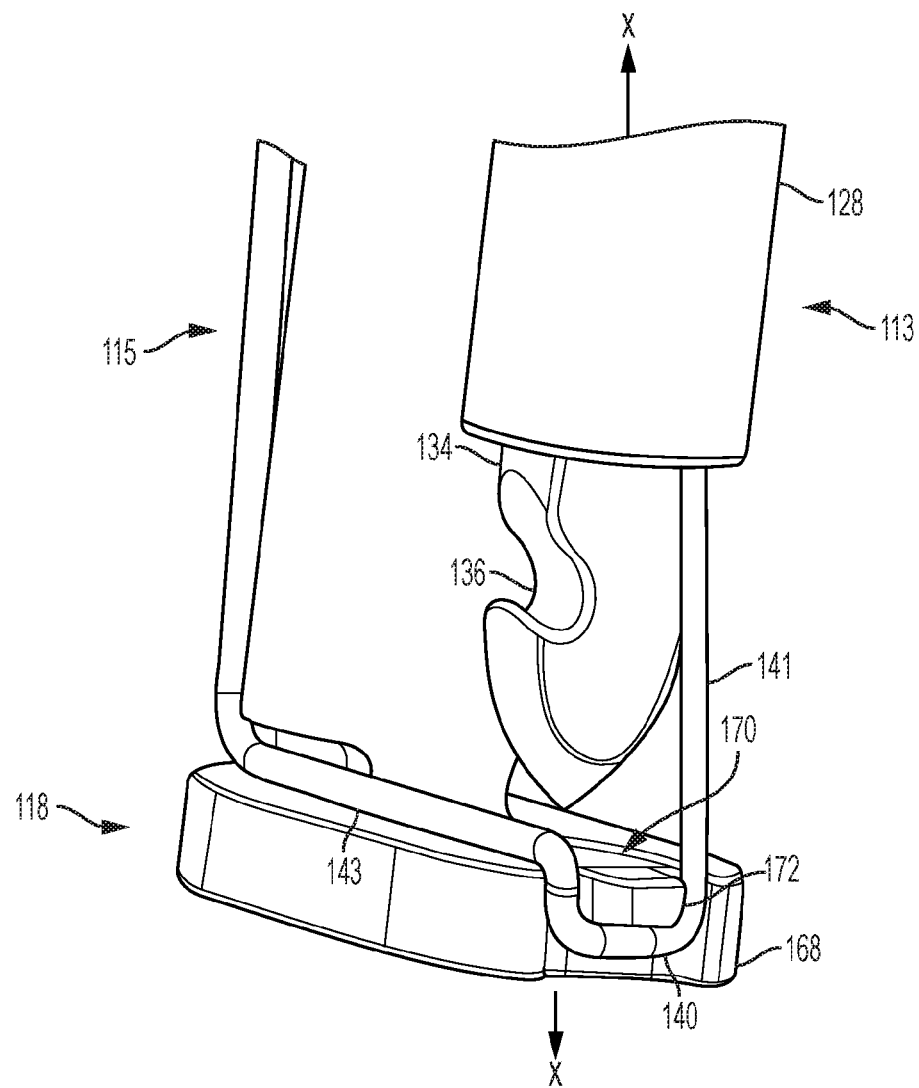
FIG. 21 a close-up perspective top view schematic representation of the needle in the unloaded configuration between the retracted and extended positions according to an alternative embodiment.

Referring now to FIG. 21, there is shown a close-up perspective top view schematic representation of the distal end 114 of the device 100 in the unloaded configuration between the retracted and extended positions according to an embodiment. After the needle 134 is fully retracted from the tissue (not shown) in FIG. 20, the needle 134 is rotated such that the notch 136 of the needle 134 faces a second direction. In one embodiment, the first direction opposes the second direction such that the needle 134 is rotated approximately 180 from the first direction to the second direction. With the notch 136 of the needle 134 facing the second direction, the needle 134 is extended through the tissue (not shown), as depicted in FIG. 21. To complete the stitch, the needle 134 is, again, extended through the aperture 170 in the end piece 168 and retracted therefrom to catch or grab the second limb 143 of suture 140 (as shown in FIG. 20 but in the opposing direction). After the notch 136 in the needle 134 catches or grabs the second limb 143 of the suture 140, the needle 134 is retracted. The needle 134 is first retracted such that the notch 136 in the needle 134 abuts the sheath 128, securing the second limb 143 of suture 140 in the notch 136. Thereafter, the needle 134 is fully retracted from the tissue to complete the stitch. As described with reference to the embodiment shown in FIGS. 1-17, the first and second limbs 141, 143 of suture 140 are withdrawn from the device, tensioned to approximate the tissue, and tied in a surgical knot formation to secure the stitch.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A suture passer, comprising:
a suture passer distal end having a body with a gripping portion and a suture holding portion;
wherein the gripping portion and the suture holding portion are spaced, defining a recess in the body therebetween;
wherein the gripping portion comprises a first tube extending along a central longitudinal axis and toward the suture holding portion and a second tube having a distal end and moveable within the first tube, wherein a distal end of the first tube comprises a lateral opening positioned therethrough, wherein the lateral opening extends at an angle to the central longitudinal axis;
a needle slidable within the second tube from a retracted position to an extended position, the needle having a notch at a needle distal end;
a rotary track extending through the suture holding portion;
wherein in the retracted position, the needle distal end is within the first tube of the gripping portion, and in the extended position, the needle distal end extends into the suture holding portion; and
wherein the suture holding portion comprises a toggle gate hingedly connected to an actuator rod, the toggle gate having a first end and being rotatable between a locked state and an unlocked state; wherein the first end of the toggle gate is configured to move in the distal direction away from the distal end of the second tube and toward the rotary track from the unlocked state to the locked state.

2. The suture passer of claim 1, wherein the suture holding portion further comprises a distal jaw having a first side and a second side with the toggle gate extending therebetween.

3. The suture passer of claim 2, wherein the toggle gate and the actuator rod are slidably disposed within the rotary track.

4. The suture passer of claim 1, wherein the second tube is tensioned toward the notch on the needle distal end.

5. The suture passer of claim 1, wherein the suture holding portion comprises an end piece having an aperture aligned within the needle such that in the extended position, the needle distal end extends into the aperture of the end piece.

6. The suture passer of claim 1, wherein the lateral opening forms a forked distal end of the first tube with a pair of opposing prongs.

7. A loaded suture passer, comprising:
a suture passer distal end of the suture passer having a body with a gripping portion and a suture holding portion;
wherein the gripping portion and the suture holding portion are spaced, defining a recess in the body therebetween;
wherein the gripping portion comprises a first tube extending along a central longitudinal axis and toward the suture holding portion and a second tube having a distal end and moveable within the first tube, wherein a distal end of the first tube comprises a lateral opening positioned therethrough, wherein the lateral opening extends at an angle to the central longitudinal axis;
a needle slidable within the second tube from a retracted position to an extended position, the needle having a notch at a needle distal end;
a rotary track extending through the suture holding portion;
wherein in the retracted position, the needle distal end is within the first tube of the gripping portion and in the extended position, the needle distal end extends into the suture holding portion;
wherein the suture holding portion comprises a toggle gate hingedly connected to an actuator rod, the toggle gate having a first end and being rotatable between a locked state and an unlocked state; wherein the first end of the toggle gate is configured to move in the distal direction away from the distal end of the second tube and toward the rotary track from the unlocked state to the locked state; and
a suture extending between a first side of the suture holding portion and a second side of the suture holding portion.

8. The suture passer of claim 7, wherein a first limb of the suture extends along a first side of the body and a second limb of the suture extends along a second side of the body.

9. The suture passer of claim 7, wherein, between the retracted position and the extended position, a first limb of suture is within the notch of the needle.

10. The suture passer of claim 9, further comprising a prong on the suture holding portion, wherein the suture is wrapped around the prong.

11. The suture passer of claim 7, wherein the suture holding portion comprises a distal jaw having a first side and a second side with the toggle gate extending therebetween.

12. The suture passer of claim 11, wherein in the locked state, the suture extends within a slot in the toggle gate.

13. The suture passer of claim 12, wherein in the unlocked state, the slot in the toggle gate is in alignment with a slot in the distal jaw such that the suture extends within the slot in the toggle gate and the slot in the distal jaw.

14. The suture passer of claim 13, wherein in the extended position, the notch of the needle is aligned with the suture which extends through the slot in the toggle gate and the slot in the distal jaw.

15. A method for passing suture through an object, the method comprising the steps of:
 providing the suture passer of claim 1;
 positioning the object having a proximal side and a distal side in the recess between the gripping portion and the suture holding portion;
 advancing the first tube and the needle through a first stitching location on the proximal side of the object to the distal side of the object;
 advancing the needle distal end into the suture holding portion;
 retracting the needle from the suture holding portion;
 catching a first limb of suture within the notch on the needle distal end; and
 retracting the needle within the second tube such that the notch on the needle distal end abuts the second tube, securing the first limb of suture within the notch.

16. The method of claim 15, further comprising the step of retracting the needle and the second tube with the first limb of suture within the notch through the proximal side of the object.

17. The method of claim 16, further comprising the steps of:
 advancing the first tube and the needle through a second stitching location on the proximal side of the object to the distal side of the object;
 advancing the needle distal end into the suture holding portion; and
 releasing the first limb of suture into the suture holding portion.

18. The method of claim 16, further comprising the steps of:
 releasing the first limb of suture on the proximal side of the object; and
 rotating the needle approximately 180 degrees.

19. The method of claim 18, further comprising the steps of:
 advancing the first tube and the needle through a second stitching location on the proximal side of the object to the distal side of the object; and
 advancing the needle distal end into the suture holding portion.

20. The method of claim 19, further comprising the steps of:
 retracting the needle from the suture holding portion;
 catching a second limb of suture within the notch on the needle distal end; and
 retracting the needle within the second tube such that the notch on the needle distal end abuts the second tube, securing the second limb of suture within the notch.

* * * * *